United States Patent [19]

Bates

[11] Patent Number: 4,927,631

[45] Date of Patent: May 22, 1990

[54] DECONGESTANT PREPARATION

[76] Inventor: Harry L. Bates, 311 West Ave., Elmira, N.Y. 14904

[21] Appl. No.: 311,983

[22] Filed: Feb. 16, 1989

Related U.S. Application Data

[63] Continuation-in-part of Ser. No. 935,937, Nov. 28, 1986, abandoned.

[51] Int. Cl.$^5$ .............................................. A61K 35/78
[52] U.S. Cl. .................. 424/195.1; 514/855; 514/969
[58] Field of Search ...................... 424/195.1; 514/855, 514/969

[56] References Cited

PUBLICATIONS

Physicians Desk Reference for Nonprescription Drugs, (1st Ed.), p. 632.

Handbook of Nonprescription Drugs, 8th Ed., Am. Phar. Assoc., Washington, D.C., pp. 550–551, 1986.

*Primary Examiner*—John W. Rollins
*Attorney, Agent, or Firm*—L. Rita Quatrini

[57] ABSTRACT

A decongestant preparation is disclosed which comprises a set of active components and a petrolatum base wherein the active components consist essentially of menthol, camphor, eucalyptus oil, and spirits of turpentine, wherein the total concentration of the active components is no greater than about 1.0% by weight of the decongestant preparation, and wherein the set of active components consists essentially of in percent by weight from about 15 to about 25 menthol, from about 30 to about 40 camphor, from about 5 to about 10 eucalyptus oil, and from about 30 to about 40 spirits of turpentine, the decongestant being suitable for direct application to the nasal cavity.

6 Claims, No Drawings

DECONGESTANT PREPARATION

This application is a continuation-in-part of application Ser. No. 935,937 which was filed Nov. 28, 1986, was abandoned.

This invention relates to a decongestant preparation which contains as active ingredients menthol, camphor, eucalyptus oil, and spirits of turpentine, and a petrolatum base, wherein the active components are present in a level of no greater than about 1% by weight. The decongestant is suitable for direct application to the nasal cavity.

BACKGROUND OF THE INVENTION

There are a number of decongestant preparations on the market today. I have not found any that work effectively in relieving severe nasal and sinus congestion. I believe that this is so because most of them are not suitable by virtue of their specific components and compositions for direct application to the nasal passages without an inhaling device such as a plastic inhaler. Rather they are used in other ways, for example by inhaling steam or their vapors, etc. An example of this is a decongestant supplied by Richardson-Vicks Inc. under the trade name of Vicks VapoRub. According to the Physicians Desk Reference For Nonprescription Drugs First Edition, page 632, Vicks VapoRub is not to be placed in the nostrils. Decongestants that are designed to be applied to the nasal passages, for example, liquid spray preparations, I have found to be irritating.

SUMMARY OF THE INVENTION

In accordance with one aspect of this invention, there is provided a decongestant preparation comprising a set of active components and a petrolatum base wherein the active components consist essentially of menthol, camphor, eucalyptus oil, and spirits of turpentine, wherein the total concentration of the active components is no greater than about 1.0% by weight of the decongestant preparation, and wherein the set of active components consists essentially of in percent by weight from about 15 to about 25 menthol, from about 30 to about 40 camphor, from about 5 to about 10 eucalyptus oil, and from about 30 to about 40 spirits of turpentine, the decongestant being suitable for direct application to the nasal cavity.

DETAILED DESCRIPTION OF THE INVENTION

For a better understanding of the present invention, together with other and further objects, advantages and capabilities thereof, reference is made to the following disclosure and appended claims in connection with the above description of some of the aspects of the invention.

This invention provides a decongestant preparation which is suitable for direct application to the nasal passages. Application in this manner results in sinus and nasal decongestion.

The decongestant of this invention is made up of a set of active componts of menthol, camphor, eucalyptus oil, spirits of turpentine, in a petrolatum base. The active components are present in the decongestant in a total concentration of no greater than about 1% by weight of the decongestant. The preferred total concentration of the active components is from about 0.3% to about 1% and most preferably from about 0.2% to about 0.5% by weight of the decongestant preparation.

The set of active components itself consists essentially of from about 15 to about 25 menthol, from about 30 to about 40 camphor, from about 5 to about 10 eucalyptus oil, and from about 30 to about 40 spirits of turpentine. Preferably the set of active components consists essentially of in percent by weight from about 19 to about 21 menthol, from about 35 to about 37 camphor, from about 8 to about 10 eucalyptus oil, and from about 34 to about 36 spirits of turpentine. Most preferably the set of active components consists essentially of in percent by weight about 20 menthol, about 36 camphor, about 9 eucalyptus oil, and about 35 turpentine.

The menthol component as used in this invention can mean menthol per se, or homologues of menthol, or combinations thereof.

The camphor component as used in this invention can mean camphor per se, or homologues of camphor, or combinations thereof.

The decongestant itself can have additional components such as aromatic oils and other ingredients. Some additional ingredients are cedar leaf oil, myristica oil, mineral oil, nutmeg oil, and thymol. The thymol component as used in this invention can mean thymol per se or homologues of thymol, or combinations thereof.

The improved decongestant of this invention can be made by mixing the desired components. An illustration of one method of making the decongestant preparation is to first make up the set of active components according to the concentrations of components given and thereafter to dilute the active components with pertrolatum to obtain the above described level of the set of active components. One typical method of preparing the decongestant of the present invention is to mix a petrolatum based preparation containing menthol, camphor, spirits of turpentine, and eucalyptus oil in which the total concentration of active components is greater than the amounts of the present invention with additional petrolatum to obtain the desired concentration of active components. One especially preferred preparation is supplied by Richardson-Vicks Inc. under the trade name of Vicks VaporRub. The composition of Vicks Vaporub is given as follows in percent by weight; about 2.6% menthol, about 4.73% camphor, about 1.2% eucalyptus oil, and about 4.5% spirits of turpentine in a petrolatum base. Other ingredients of Vick Vaporub are cedar leaf oil, myristica oil, mineral oil, nutmeg oil, and thymol. A preferred source of the petrolatum is petroleum jelly supplied by Chesebrough-Ponds Inc. under the trade name of Vaseline. Specific amounts will be apparent in the Example that follows.

The petrolatum component acts as a diluent for the other components. By virtue of the high dilution of the active ingredients with the petrolatum, the preparation can be applied directly to the nasal cavity without causing irritation of the nasal cavity by the active ingredients and other ingredients. The petrolatum serves also to aid in expulsion of congesting mucous and fluids from the sinuses and nasal cavity.

To more fully illustrate this invention, the following non-limiting example is presented.

EXAMPLE

About 1 part be weight of Vicks VaporRub is mixed with about 52 parts by weight of Vaseline as the source of petrolatum and applied to the nasal passages several times a day. This results in opening up of the nasal passages and expulsion of mucous from the sinuses.

While there has been shown and described what are at present considered to preferred embodiments of the invention, it will be obvious to those skilled in the art that various changes and modifications may be made therein without departing from the scope of the invention as defined by the appended claims.

What is claimed is:

1. A decongestant preparation comprising a set of active components and a petrolatum base wherein said active components consist essentially of menthol, camphor, eucalyptus oil, and spirits of turpentine, wherein the total concentration of said active components is no greater than about 1.0% by weight of said decongestant preparation, and wherein said set of active components consists essentially of in percent by weight from about 15 to about 25 menthol, from about 30 to about 40 camphor, from about 5 to about 10 eucalyptus oil, and from abut 30 to about 40 spirits of turpentine, said decongestant being suitable for direct application to the nasal cavity.

2. A decongestant of claim 1 wherein the total concentration of said active components is from about 0.3% to about 1/0% by weight of said decongenstant preparation.

3. A decongestant of claim 2 wherein the total concentration of said active components is from about 0.2% to about 0.5% by weight of said decongestant preparation.

4. A decongestant of claim 1 wherein said set of active components consists essentially of in percent by weight from about 19 to about 21 menthol, from about 35 to about 37 camphor, from about 8 to about 10 eucalyptus oil, and from about 34 to about 36 spirits of turpentine.

5. A decongestant preparation of claim 1 wherein said decongestant preparation contains as additional components one or more aromatic oils.

6. A decongestant preparation of claim 1 wherein said decongestant preparation contains as additional components at least one member selected from the group consisting of cedar leaf oil, myristica oil, mineral oil, nutmeg oil, and thymol.

* * * * *